US011644442B2

United States Patent
Xiang et al.

(10) Patent No.: US 11,644,442 B2
(45) Date of Patent: May 9, 2023

(54) SYSTEM AND METHOD FOR NANOSCALE PHOTOACOUSTIC TOMOGRAPHY

(71) Applicant: The Board of Regents of the University of Oklahoma, Norman, OK (US)

(72) Inventors: Liangzhong Xiang, Norman, OK (US); Jian Chen, Norman, OK (US); Pratik Samant, Norman, OK (US)

(73) Assignee: The Board of Regents of the University of Oklahoma, Norman, OK (US)

(*) Notice: Subject to any disclaimer, the term of this patent is extended or adjusted under 35 U.S.C. 154(b) by 1250 days.

(21) Appl. No.: 16/088,770

(22) PCT Filed: Mar. 31, 2017

(86) PCT No.: PCT/US2017/025474
§ 371 (c)(1),
(2) Date: Sep. 26, 2018

(87) PCT Pub. No.: WO2017/173330
PCT Pub. Date: Oct. 5, 2017

(65) Prior Publication Data
US 2019/0170695 A1  Jun. 6, 2019

Related U.S. Application Data

(60) Provisional application No. 62/316,837, filed on Apr. 1, 2016.

(51) Int. Cl.
*G01N 29/06* (2006.01)
*G01N 21/17* (2006.01)
(Continued)

(52) U.S. Cl.
CPC ....... *G01N 29/0672* (2013.01); *A61B 5/0095* (2013.01); *A61B 5/02007* (2013.01);
(Continued)

(58) Field of Classification Search
CPC .......... G01N 29/0672; G01N 21/1702; G01N 29/2418; G01N 2021/1706;
(Continued)

(56) References Cited

U.S. PATENT DOCUMENTS 7,176,450 B2   2/2007 Hollingsworth
8,041,162 B2  10/2011 Wang et al.
(Continued)

FOREIGN PATENT DOCUMENTS

JP    2008194106 A  *  8/2008
WO   WO-2018015663 A1 *  1/2018  ............ G01J 3/2823

OTHER PUBLICATIONS

Yao, Da-Kang, et al.; "Optimal Ultraviolet Wavelength for in vivo Photoacoustic Imaging of Cell Nuclei"; Journal of Biomedical Optics; vol. 17(5); May 2012; 8 pages.
(Continued)

*Primary Examiner* — Lisa M Caputo
*Assistant Examiner* — Rose M Miller
(74) *Attorney, Agent, or Firm* — Conley Rose, P.C.; Grant Rodolph; Jonathan K. Polk

(57) ABSTRACT

A method and system of nanoscale photoacoustic tomography (nPAT) for non-invasive three-dimensional mapping and characterization of fine cellular structures (such as but not limited to organelles, vesicles, and macromolecules) of biological samples is disclosed.

28 Claims, 10 Drawing Sheets

(51) Int. Cl.
*G01N 29/24* (2006.01)
*A61B 8/13* (2006.01)
*A61B 5/00* (2006.01)
*A61B 5/02* (2006.01)
*G01N 29/22* (2006.01)

(52) U.S. Cl.
CPC ....... *G01N 21/1702* (2013.01); *G01N 29/221* (2013.01); *G01N 29/223* (2013.01); *G01N 29/2418* (2013.01); *A61B 8/13* (2013.01); *A61B 2562/0285* (2013.01); *G01N 2021/1706* (2013.01); *G01N 2201/06113* (2013.01); *G01N 2291/02466* (2013.01)

(58) Field of Classification Search
CPC .......... G01N 2201/06113; G01N 2291/02466; G01N 29/221; G01N 29/223; A61B 5/0095; A61B 5/02007; A61B 8/13; A61B 2562/0285
USPC .......................................................... 367/7
See application file for complete search history.

(56) References Cited

U.S. PATENT DOCUMENTS

| | | | |
|---|---|---|---|
| 8,814,794 B2 | 8/2014 | Oishi | |
| 8,879,352 B2 | 11/2014 | Witte et al. | |
| 8,997,572 B2 | 4/2015 | Wang et al. | |
| 9,335,253 B2* | 5/2016 | Ode | G01N 29/0672 |
| 9,439,571 B2 | 9/2016 | Wang et al. | |
| 9,528,966 B2 | 12/2016 | Wang et al. | |
| 9,587,976 B2 | 3/2017 | Wang et al. | |
| 9,655,527 B2 | 5/2017 | Wang et al. | |
| 9,833,148 B2 | 12/2017 | Wang | |
| 10,070,813 B2 | 9/2018 | Wang et al. | |
| 10,955,335 B2* | 3/2021 | Pelivanov | G01N 21/1702 |
| 2007/0187632 A1 | 8/2007 | Igarashi | |
| 2009/0296102 A1* | 12/2009 | Tamura | A61B 5/0066 356/512 |

OTHER PUBLICATIONS

Dehoux, T., et al.; "All-Optical Broadband Ultrasonography of Single Cells"; Scientific Reports; vol. 5; Mar. 3, 2015; 5 pages.

Strohm, Eric M., et al.; "High Frequency Label-Free Photoacoustic Microscopy of Single Cells"; Photoacoustics; vol. 1; Dec. 2013; 5 pages.

PCT International Search Report; Application No. PCT/US2017/025474; dated Jun. 16, 2017; 3 pages.

PCT Written Opinion of the International Searching Authority; Application No. PCT/US2017/025474; dated Jun. 16, 2017; 14 pages.

* cited by examiner

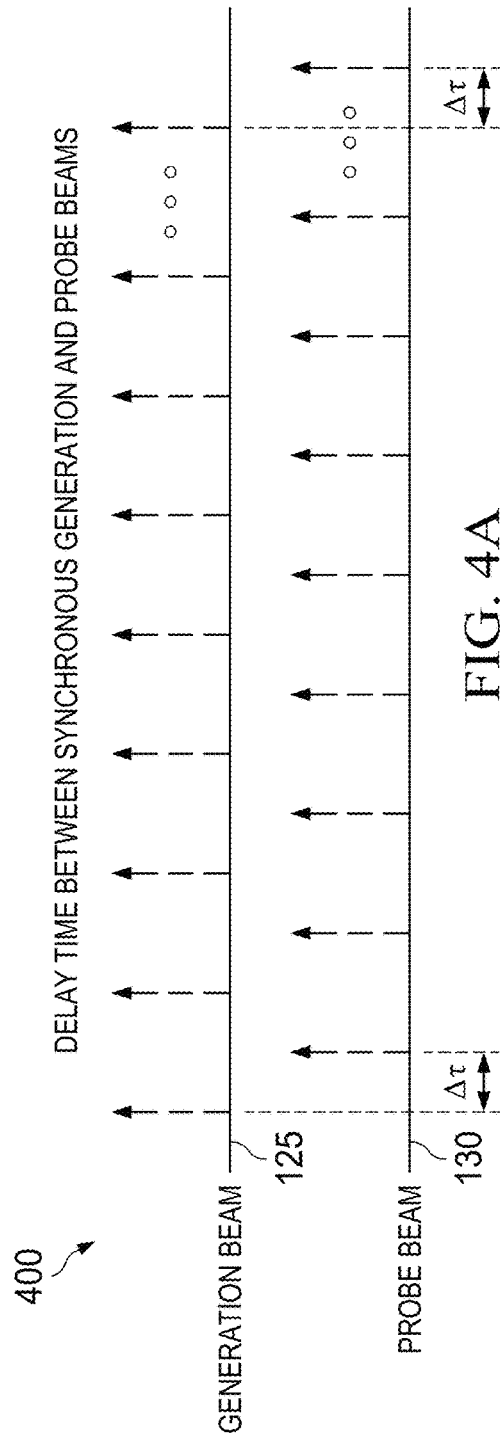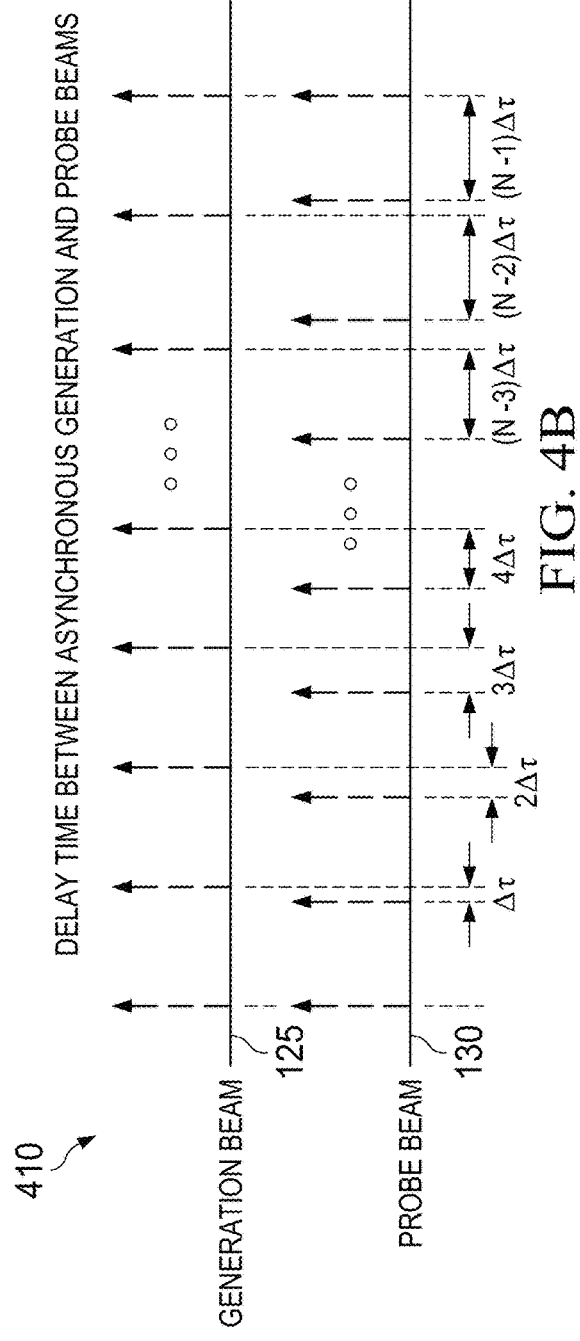

SYSTEM AND METHOD FOR NANOSCALE PHOTOACOUSTIC TOMOGRAPHY

CROSS-REFERENCE TO RELATED APPLICATIONS

This application is a national stage application of international patent application number PCT/US2017/025474 filed on Mar. 31, 2017 by The Board of Regents of the University of Oklahoma and titled "System and Method for Nanoscale Photoacoustic Tomography," which claims priority to U.S. provisional patent application No. 62/316,837 filed on Apr. 1, 2016 by The Board of Regents of the University of Oklahoma and titled "System and Method for Nanoscale Photoacoustic Tomography," both of which are incorporated herein by reference.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Cancers are a serious hazard to human health with high mortality rates relative to other diseases. Their treatment is a challenging issue that remains unsolved. An effective way to increase survival rate is early-stage examination and diagnosis, gaining deep knowledge of carcinogens at micro/nanoscales. Cells are constituents of all biological tissues, and their structural changes are associated with the emergence and development of a number of high-mortality diseases. For example, irregular shapes and large sizes of cell nuclei are two morphological characteristics of cancer cells, which can be considered hallmarks of cancer and are used by pathologists to determine cancer grade and evaluate prognosis. Understanding such changes, in addition to functional and mechanical irregularities, is crucial for disease diagnosis and cell state monitoring. Therefore, non-invasiveness, label free functionality, and high-resolution cellular imaging capabilities are of importance. The current lack of high spatial resolution correlated to the local subsurface is a major drawback, preventing high-fidelity analysis and interpretation of the structural components within cells. To gain a deeper knowledge of cellular architecture, nanoscale tomography is crucial.

Until now, several optical methods such as reflectance confocal microscopy, fluorescence confocal microscopy, and multiphoton microscopy have been used to successfully image cell nuclei without sectioning. However, they fall short of a label-free method with high contrast and spatial resolution in the z-direction. PAM is a label-free imaging technique that explores endogenous optical absorbers like DNA, RNA, hemoglobin, and melanin, and it has been successfully applied to imaging of cells. In PAM, the laser spot is tightly focused in the lateral direction, but less so in the axial direction. The axial resolution is limited by the bandwidth of the ultrasound transducer, and can be many times larger than the lateral resolution, typically greater than 25 µm. Moreover, photoacoustic waves generated from micron sized objects, such as DNA/RNA, are usually above 100 MHz. Therefore, a large portion of the photoacoustic signal energy is not recorded when using transducers with central frequency less than 100 MHz, and the measurement SNR is reduced. To achieve high axial resolution of photoacoustic imaging, photoacoustic microscopy using high frequency transducers up to ~1.2 GHz is also applied at room temperature, offering typical resolutions of ~1 µm using water as the coupling medium. But even at these frequencies it is difficult to distinguish the fine structure of cells.

Recently, a time-resolved opto-acoustic technique, dubbed picosecond ultrasonics, was applied to single cell imaging, operating in the 10-100 GHz frequency range, allowing the mapping of cell structures as thin as 10 nm and resolving fine details. This technique enables derivation of important physical values of cells, such as thickness, sound velocities, bulk moduli, and ultrasonic attenuation coefficients. It should also be invaluable for investigating the mechanical properties of intra-cellular organelles. However, such studies are based on ultrasonography and cannot probe endogenous optically absorbing components of cells, which could reveal rich optical contrasts according to chemical composition and provide unique opportunities to image and analyze single cells. New non-invasive methods for analyzing single cells and subcellular components would be desirable.

BRIEF DESCRIPTION OF THE DRAWINGS

Several embodiments of the present disclosure are illustrated in the appended drawings. It is to be noted, however, that the appended drawings only illustrate several typical embodiments and are therefore not intended to be considered limiting of the scope of the present disclosure. The figures are not necessarily to scale and certain features and certain views of the figures may be shown as exaggerated in scale or in schematic in the interest of clarity and conciseness.

FIG. 4A is a graph of a time delay between synchronous generation beams and probe beams.

FIG. 4B is a graph of a time delay between asynchronous generation beams and probe beams.

DETAILED DESCRIPTION

Figure 1:
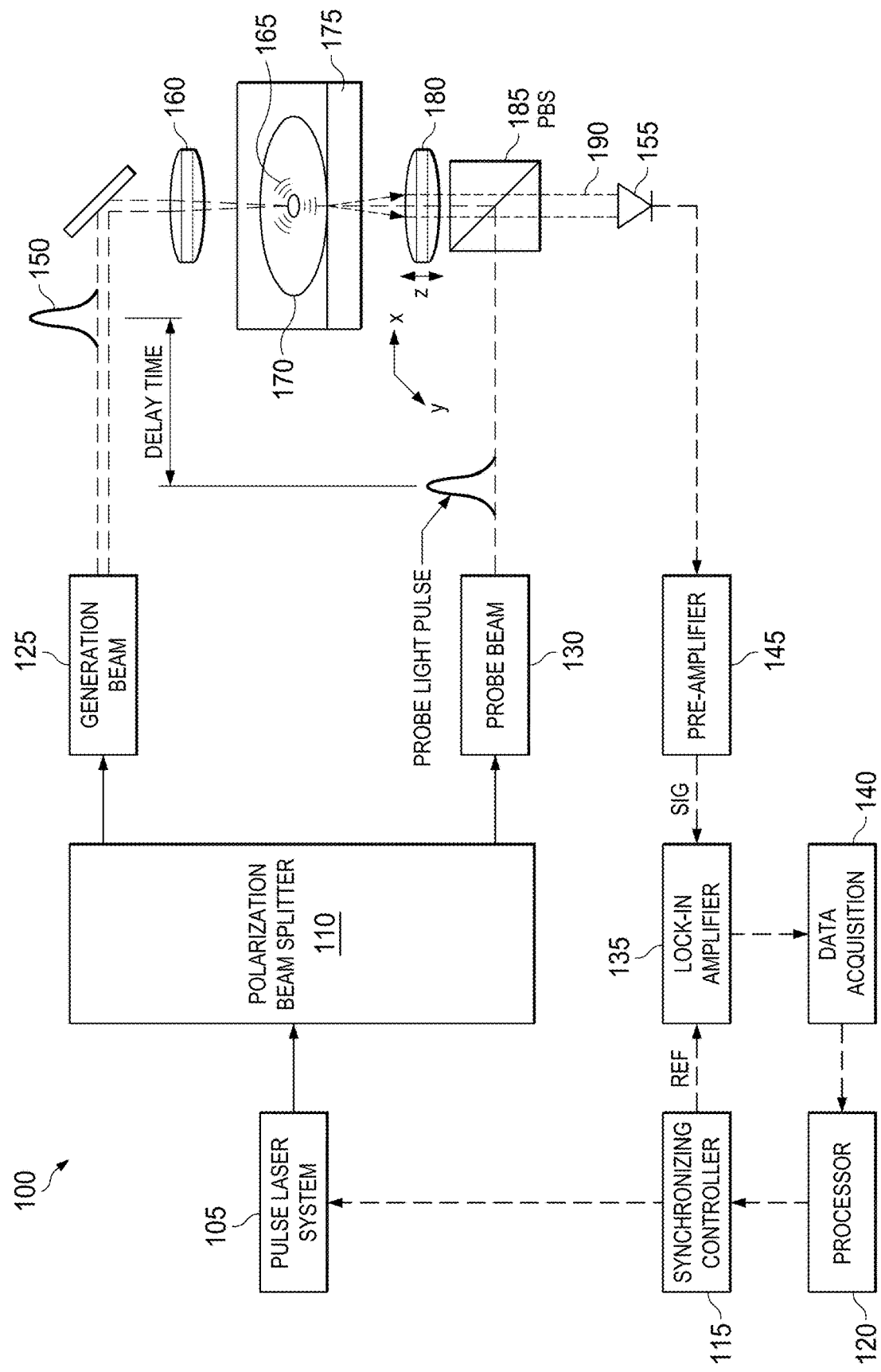
FIG. 1 is a schematic of an embodiment of a nPAT system according to the present disclosure.

A method and system of nPAT for non-invasive three-dimensional mapping and characterization of fine cellular structures and components (such as but not limited to organelles, vesicles, and macromolecules) of biological samples is disclosed. Examples of such cellular structures and components include, but are not limited to, melanosomes, DNA and/or RNA in cell nuclei, and proteins, such as for example, hemoglobin in red blood cells is disclosed. The method may be label-free. In certain embodiments the optical absorption properties of samples are imaged in three dimensions with nanometer-scale spatial resolution, in which an ultrafast pulsed laser is used to generate photoacoustic waves and to detect changes in surface light reflectivity, which are representative of features of the sample. For example, a ps-pulsed or fs-pulsed laser may be used to generate and detect the high frequency photoacoustic waves, up to tens of GHz. In disease diagnosis and cell biology, the disclosed method and system provide not only morphological information, but also functional and molecular imaging information. For example, morphological and optical contrast information can assess concentrations and changes of biological substances in localized areas in the specimen with both high sensitivity and high specificity, enabling the effective use of photoacoustic imaging as diagnostic at the sub-cell scale.

Before describing various embodiments of the present disclosure in more detail by way of exemplary description, examples, and results, it is to be understood that the present disclosure is not limited in application to the details of methods and compositions as set forth in the following description. The present disclosure is capable of other embodiments or of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the embodiments of the present disclosure may be practiced without these specific details. In other instances, features which are well known to persons of ordinary skill in the art have not been described in detail to avoid unnecessary complication of the description.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which the present disclosure pertains.

All patents, published patent applications, and non-patent publications referenced in any portion of this application are herein expressly incorporated by reference in their entirety to the same extent as if each individual patent or publication was specifically and individually indicated to be incorporated by reference.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error Further, in this detailed description, each numerical value (e.g., temperature or time) should be read once as modified by the term "about" (unless already expressly so modified), and then read again as not so modified unless otherwise indicated in context. As noted, any range listed or described herein is intended to include, implicitly or explicitly, any number within the range, particularly all integers, including the end points, and is to be considered as having been so stated. For example, "a range from 1 to 10" is to be read as indicating each possible number, particularly integers, along the continuum between about 1 and about 10. Thus, even if specific data points within the range, or even no data points within the range, are explicitly identified or specifically referred to, it is to be understood that any data points within the range are to be considered to have been specified, and that the inventors possessed knowledge of the entire range and the points within the range. The use of the term "about" may mean a range including ±20%, or ±15%, or ±10% of the subsequent number unless otherwise stated.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

The terms "biological sample" and "biological specimen" may be used interchangeably herein.

The following abbreviations and initialisms apply:
ANSI: American National Standards Institute
BBO: beta barium borate
DBM: double-balanced mixer
DM: dichroic mirror
DNA: deoxyribonucleic acid
FEM: finite element method
fs: femtosecond(s)
FWHM: full width at half maximum
GHz: gigahertz
HW: half wave
InGaAs: indium gallium arsenide
K: Kelvin
MHz: megahertz
mJ/cm$^2$: millijoule(s) per centimeter square
mm: millimeter(s)
m/s: meter(s) per second
NA: numerical aperture
nJ: nanojoule(s)
nm: nanometer(s)
nPAT: nanoscale PAT
PAM: photoacoustic microscopy
PAT: photoacoustic tomography
PBS: polarization beam splitter
pJ: picojoule(s)
PRF: pulse repetition frequency
ps: picosecond(s)
QW: quarter wave
RBC: red blood cell
RNA: ribonucleic acid
SNR: signal-to-noise ratio
WD: working distance
μm: micrometer(s).

In non-limiting embodiments of the nPAT system disclosed herein, a generation beam from an ultrafast laser source with ultrashort duration (e.g., on the order of picoseconds or femtoseconds) may be used to illuminate the biological specimen under analysis. The light is absorbed by molecules in the specimen, such as DNA and RNA, and converted to heat causing, as a result of thermoelastic expansion, high frequency photoacoustic waves (e.g., up to tens of GHz) which propagate outwardly. When the photoacoustic waves arrive at the surface of the specimen, they induce reflectance changes via elasto-optic coupling, which can be detected by a separate probe beam. The time-resolved history of the photoacoustic waves is recorded by adjusting the delay time between the generation and probe beams, with temporal resolution up to several femtoseconds. In addition, based on raster scanning (typically having a step size of $\lambda/2$), a three dimensional nanoscale tomographic image can be reconstructed from the amplitude envelopes of photoacoustic signals, presenting both morphological and functional information. Therefore, the presently disclosed system and method allow for the study of subcellular structures with high sensitivity, and high spatial resolution in both lateral and axial directions.

In certain embodiments, to gain a deeper knowledge of intact subcellular architecture, a biological specimen can be imaged ex vivo with the nPAT system and method with nanometer resolution. It enables three dimensional imaging of endogenous biological and biochemical substances in localized areas in the specimen including, but not limited to, DNA/RNA, glucose, hemoglobin, lipids, melanin, and cytochromes. The morphological and spatially distributed optical information can be used for noninvasive, label-free and nanoscale spatial measurements, providing high-fidelity analysis and interpretation of the structural components within cells for use in disease diagnosis, for example. Moreover, the nPAT system is all-optics, non-contact based, thereby avoiding severe attenuation of high-frequency photoacoustic waves in the coupling medium, which is important in conventional photoacoustic microcopy and tomography.

A non-limiting embodiment of the nPAT system 100, illustrated in FIG. 1, includes for example, (a) an ultrafast pulse laser system 105 for providing a generation beam 125 for generating photoacoustic waves in a biological specimen 170, and a probe beam 130 for assessing changes in light reflectivity in the biological specimen 170 caused by the photoacoustic waves, (b) a scanning stage 175 upon which the biological specimen 170 can be mounted for analysis, (c) a first focusing assembly (e.g., first objective lens) 160 for focusing the generation beam 125 on the biological specimen 170, (d) a second focusing assembly (e.g., second objective lens) 180 for focusing the probe beam 130 on the biological specimen 170 and for collecting backscattered light reflected from the biological specimen 170, (e) an optical detector 155 for sensing the backscattered light and emitting signals in response thereto, and (f) a processor 120 configured with a reconstruction algorithm to record and process the signals from the optical detector 155 into tomographic images of the sample. The generation beam 125 and the probe beam 130 can be emitted from the same laser or a different pulse laser. The selection of laser wavelength depends on the imaging purpose, specifically the biological specimens to be studied, for example 532 nm wavelength for RBCs. Through free space or optical fiber bundles, laser light may be delivered to the biological specimen 170, for example, with an energy density below the ANSI safety limit, 20 mJ/cm$^2$.

Any equipment or/and apparatus suitable for emitting ultra-short laser pulses for microscopy can be used in the nPAT system disclosed herein. For example, in one embodiment a generation beam may be emitted using a Complier 1064/532/266 nm, a diode-generation solid-state 5-ps pulse laser with re-switchable outputs and commercially available from Passat (Toronto, Canada). Suitable light pulse durations include, but are not limited to, those in a range of about 10 fs to about 100 ps, to generate high frequency photoacoustic waves up to tens of GHz. To avoid thermal damage to the specimen, such as from ablation or overheating, the generation beam may be attenuated to approximate energy using a neutral density filter. The measuring unit may include an optical detection system and an optical detector for detecting and recording signals from the biological specimen under study. The optical detection system may include, for example, (a) a probe beam for sensing the reflectance change, (b) an objective lens, which is placed close to the biological specimen for focusing the probe beam and for collecting backscattered (reflected) light from the biological specimen, and (c) an optical detector for recording the backscattered light and providing signals in response to the backscattered light. The backscattered light enters the optical detector, and the reflectance of the specimen surface is after precisely the delay time has elapsed following photoacoustic wave generation. In one non-limiting embodiment, an InGaAs photodiode is used as the detector (for example, DET10 N, commercially available from Thorlabs, (Austin, Tex.)). The output signal of the detector may be fed to a preamplifier.

To ensure measurement accuracy and amplify the extremely small signal variations of light intensity due to reflectance change that compared with the fluctuations of the laser source, a lock-in amplifier may be utilized, which performs phase-sensitive detection of the signals. In one embodiment, the lock-in amplifier SR865 from Stanford may be used. The output of the lock-in amplifier may be communicated to a control system, which includes a processor and data acquisition. The processor may be used to control the time delay adjusting, record and process the photoacoustic signal, and reconstruct photoacoustic images. Herein, a "processor" may refer to any suitable device operable to execute instructions and manipulate data, e.g., personal computer, work station, laptop, handheld device, network computer, or any other suitable processing device.

To synchronize the nPAT system, a synchronizing controller may be used. The synchronized signal from the controller can be used to trigger the laser emission and as a reference signal of lock-in amplifier. Meanwhile, it can be used to trigger data acquisition and the mechanical scanning.

Figure 2:
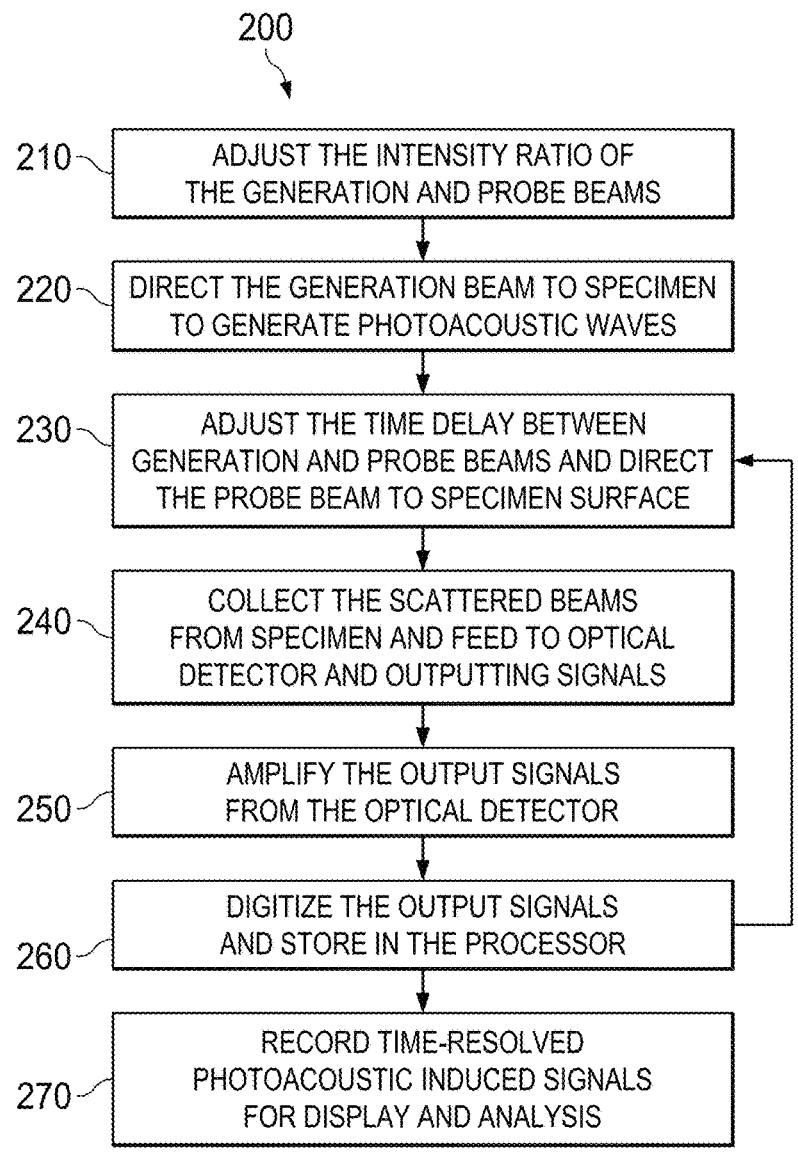
FIG. 2 is a flowchart which depicts an nPAT method for analysis of a specimen.

FIG. 2 is a flowchart of a method 200 for time-resolved measurement of photoacoustic signals at a specific point of the biological sample in accordance with at least one embodiment of the present disclosure. The nPAT system 100 implements the method 200. At step 210, the intensity ratio of the generation beam 125 and the probe beam 130 is adjusted. The ratio may be set to 10, for example, the energies of generation and probe pulses are 0.5 nJ and 50 pJ, respectively. At step 220, the generation beam 125 is directed to the biological sample 170 for generating the photoacoustic waves, and various means of generating photoacoustic waves may be envisaged. At step 230, a time delay is introduced between the generation beam 125 and the probe beam 130 such that the probe beam 130 arrives at the biological sample 170 surface after the generation beam 125 is applied to the biological sample 170. The photoacoustic wave is monitored by the probe beam 130 via elasto-optic coupling. When the photoacoustic wave arrives at the biological sample surface, it induces a surface reflectivity change, and the acoustic vibration is modulated by the probe beam 130. At step 240, the scattered probe beam is collected by an optical assembly (e.g. a microscopic objective lens or a lens assembly including the first focusing assembly 160 and the second focusing assembly 180) and sent to the optical detector 155 (e.g., a photodiode) for sensing. The signal variations of light intensity due to the reflectivity change of the specimen are very small, even compared with the fluctuation of the laser source. At step 250, the acquired signals from the photodiode output may be amplified with the help of a lock-in amplifier. However, various methods for measuring very small signals may be envisaged. At step 260, the control system is used to digitize, process, and store the measured signals and control the measurement procedures. It may determine an action from interpretation to continue or terminate the measurement. By iteratively tuning the delay time between the generation and probe beams and recording corresponding signals, at step 270 a time-resolved photoacoustic signal is measured and stored. It can then be displayed and analyzed by the processor 120.

By raster scanning the specimen and recording the time-resolved photoacoustic signal at each scanning point, three dimensional information of the specimen can be stored and three dimensional PAT images can then be reconstructed based on the acquired data.

Figure 3A:
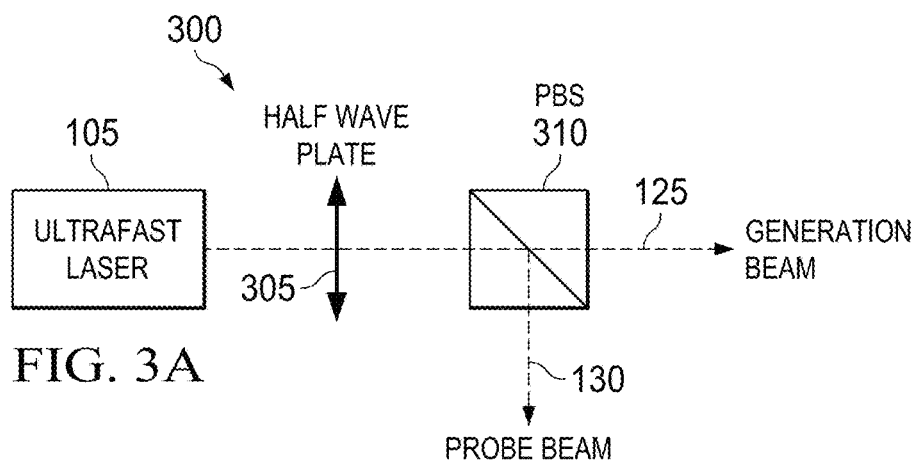
FIG. 3A is a schematic of a system for forming synchronous generation beams and probe beams of the same wavelength.
Figure 3B:
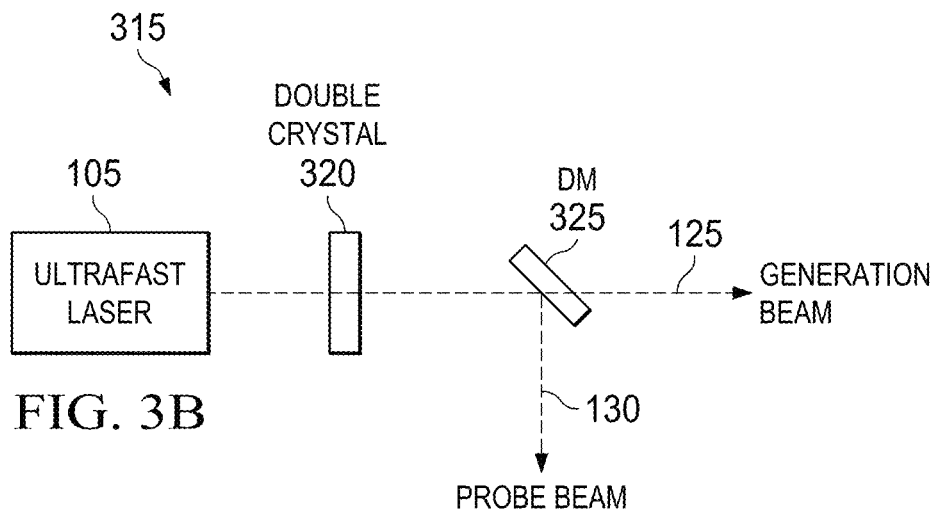
FIG. 3B is a schematic of a system for forming synchronous generation beams and probe beams of different wavelengths.
Figure 3C:
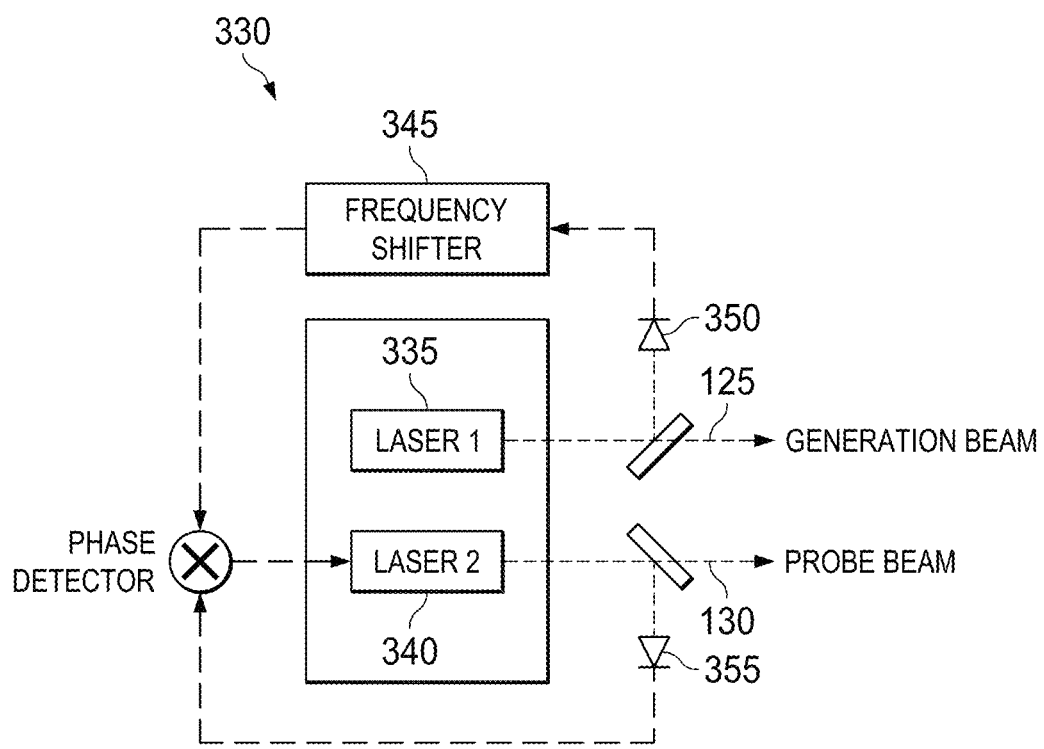
FIG. 3C is a schematic of a system for forming asynchronous generation beams and probe beams of different wavelengths.

The formation of the generation beam and the probe beam based on different laser configurations are shown in FIGS. 3A-3C. In FIG. 3A, a first type 300 of generation beam 125 and probe beam 130 is synchronous and of the same wavelength. The laser beam is firstly transmitted through an HW plate 305 forming a polarized beam, wherein the beam polarization is controlled by rotating the HW plate 305. The polarized beam is then divided into a generation beam 125 and a probe beam 130 with a PBS 310. The generation beam 125 is s-polarized and transmitted through the PBS 310 directly, while the probe beam 130 is reflected by the PBS 310 with p-polarization. Meanwhile, the ratio between s-polarized generation beam 125 and p-polarized probe beam 130 can be set by rotating the HW plate 305 to change the beam polarization after passing through it.

In FIG. 3B, a second type 315 of generation beam 125 and probe beam 130 formation is also synchronous, but the wavelength is different. The emitted laser beam enters a double crystal 320 to produce a second harmonic beam with specified conversion efficiency. For example, a BBO crystal may be used to produce second harmonic 266 nm pulses with 10% conversion efficiency from a 532 nm source. The fundamental and second-harmonic beams are then split by a DM 325. The transmitted fundamental beam serves as the generation beam 125 with higher power, and the second-harmonic beam is reflected by the DM as the probe beam 130. Compared to the first type, the intensity ratio between the generation beam 125 and the probe beam 130 is fixed and is related to the conversion efficiency of the double crystal 320.

In FIG. 3C, a third type 330 of generation beam 125 and probe beam 130 is asynchronous, wherein each beam is from a different laser source 335, 340 and may have a different wavelength. In this scheme, the PRF of the generation beam 125 and the probe beam 130 are slightly different, and can be controlled by a frequency shifter 345, which may comprise a single-sideband generator. To achieve this, the PRF of both lasers 335, 340 is measured with a fast photodiode 350, 355, and the PRF of laser 1 335 is upshifted using a frequency shifter 345. Then, the PRF of laser 2 340 is phase locked to the frequency shifted repetition with a DBM as a phase detector. The output beam of laser 1 335 serves as the generation beam 125, whereas the laser beam from laser 2 340 with upshifted PRF serves as the probe beam 130. The intensity of the generation beam 125 and the probe beam 130 can be adjusted or attenuated separately.

The time delay between the generation beam and probe beams can be scanned with a preset interval to record the time history of the photoacoustic wave at a specified point, which is named the A-scan signal. FIGS. 4A-B illustrate the time delay for both synchronous and asynchronous generation beams 125 and probe beams 130. For the synchronous generation beam 125 and probe beam 130, the time delay can be set by a delay time adjusting unit, which may comprise an optical system that adjusts the optical path length by physically moving the position of mirrors placed on the probe beam 130 path. The delay time is calculated to be $\Delta t = \Delta L/c$, where $\Delta L$ is the optical path difference between the generation beam 125 and the probe beam 130, and c is the speed of light. By mechanically adjusting the optical path length of the probe beam 130, the time delay $\Delta t$ will be set.

The movable mirrors may be a pair of reflecting mirrors placed at the angle of 45 degrees against the probe (incident) beam axis and mounted on the mechanical scanning stage. In addition, a pair of fixed reflecting mirrors may be used to align the probe beam 130 parallel to the translation stage axis. The input probe beam 130 is reflected by one of the reflecting mirrors in the direction perpendicular to the incident beam axis, hits the other reflecting mirror, and is reflected by another reflecting mirror in the direction parallel to the incident direction. In at least one embodiment, the movable mirrors may be mounted on the translation stage's V-block which contains two kinematic mirror mounts and two irises for beam alignment. If the translation stage is at minimum position, the optical path length of the probe beam 130 equals to that of the generation beam, and the delay time is $\Delta t = 0$. When the translation stage is moving towards its maximum position, the optical path length of the probe beam 130 becomes longer. As a result, the time delay of the probe beam 130 with respect to the generation beam 125 could be set by moving the stage. In one sample embodiment, a long-travel, low-profile direct drive stage (e.g., DDS220 from Thorlabs) is used. The travel range of the stage in one embodiment is 220 mm, so the maximum optical path length of the probe beam is 440 mm, capable of tuning the optical delay up to 1466 ps. The absolute position of the stage is determined using a high-resolution, closed-loop optical feedback signal that provides bidirectional repeatability of 0.25 µm, and the timing repeatability of 1.67 fs could be achieved.

In addition to the time delay adjusted by the mechanical translation stage for the synchronous generation beam 125 and probe beam 130 pulses, an alternative may be implemented based on asynchronous generation beam 125 and probe beam 130 from two pulse lasers with slightly different repetition frequencies. Supposing the fundamental repetition frequency of both lasers is $f_m$, and the repetition frequency of the generation laser is downshift by $\Delta f$, the period of generation pulse train is calculated to be $\Delta t_1 = 1/(f_m - \Delta f)$, and that of the probe pulse train is $\Delta t_2 = 1/f_m$. With each pulse, the delay time between the generation beam 125 and the probe beam 130 would increase by $\Delta t_s = \Delta t_1 - \Delta t_2 = \Delta f/(f_m(f_m - \Delta f))$. By synchronizing the starting pulses of the generation beam 125 and the probe beam 130 as shown in FIG. 4B, the delay time $\Delta t$ should be $(n-1)\Delta t_s$ at the nth sampling, where $0 < n \leq N$. The maximum sample number is determined as $N = \Delta t_1/\Delta t_s$, after which the generation beam 125 and probe beam 130 pulse are overlapping again. Therefore, the maximum tuning of the optical delay time is $\Delta t_1$. For example, if the fundamental repetition frequency $f_m = 50$ MHz, and the frequency shifter $\Delta f = 500$ Hz, the tuning resolution $\Delta t_s$ should be 200 fs, the maximum optical delay is 20 ns. The time for one sampling cycle is determined by the frequency shifter $\Delta f$, and equals to $1/\Delta f$. By tuning the frequency shifter, the time resolution and acquisition time can be adjusted. However, the maximum delay time is fixed by the fundamental repetition frequency of the laser.

Figure 5:
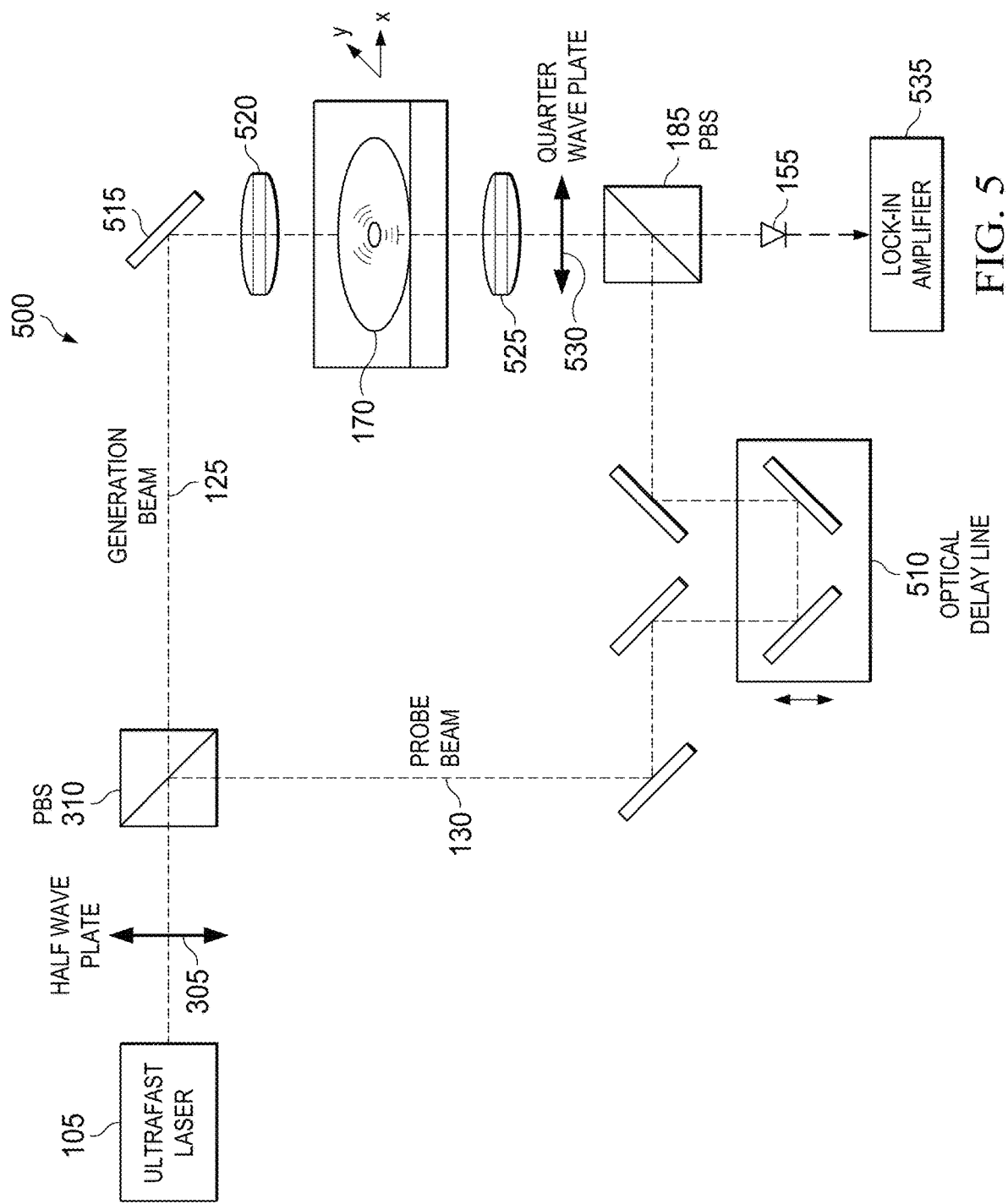
FIG. 5 shows a schematic of an embodiment of an nPAT system which forms synchronous generation and probe beams having the same wavelength.

FIG. 5 shows the configuration of one non-limiting embodiment of an nPAT system 500 with the first type of generation beam 125 and probe beam 130 (synchronous and of the same wavelength). In this embodiment, the nPAT system 500 is assembled in a transmission configuration. The generation beam 125 is directed and focused by a microscopic objective lens (e.g., first focusing assembly) 520 onto the biological specimen 170 to generate photoacoustic waves via an optical delivering system. In one embodiment, the generation beam 125 is reflected by a reflecting mirror 515 and focused into a nearly diffraction-limited spot by the microscopic objective lens 520 (e.g., 50× Mitutoyo Plan Apo Infinity corrected long WD objective, commercially available from Edmund Optics Inc. (Barrington, N.J.)). The spot size is determined by both the illuminating wavelength $\lambda$ and the NA of the microscopic objective lens 520, and the diameter of the spot is approximately $0.85\lambda/NA$. In the photoacoustic phenomenon, the spatially-distributed optical energy is absorbed by biological substances (i.e., optical light is absorbed by molecules) and converted to heat. Proportionate photoacoustic waves are generated due to the subsequent thermoelastic expansion. The photoacoustic waves are then detected and recorded by the measuring unit.

As in the case shown in FIG. 5, the measuring unit includes (1) a probe beam 130 for sensing the reflectance change with adjustable optical path length, (2) an objective lens (e.g., second focusing assembly) 525, which is placed close to the biological specimen 170 for focusing the probe beam 130 and collecting backscattered light from the biological specimen 170, (3) a combination of the PBSs 310 and a QW plate 530 for separating the incident and backscattered light, and (4) the optical detector 155 for recording the backscattered light. The probe beam 130 is p-polarized and deflected by the PBS 185 towards the biological specimen 170. The QW plate 530 is inserted between the objective lens 525 and the PBS 185. When the backscattered light passes through the QW plate 530, the polarization of the backscattered probe beam 130 changes to s-polarization since it has passed the QW plate 530 twice, and transmits through the PBS 185 directly. The backscattered light from the probe beam 130 then enters the optical detector 155, and the reflectance of the biological specimen 170 surface is recorded after an elapsed delay time. The output signal of the optical detector 155 is then fed to the signal channel of a lock-in amplifier 535. By manually tuning or automatically scanning an optical delay line 510, and recording the output of the lock-in amplifier 535, a time-resolved photoacoustic signal is measured and stored.

Suitably, the generation beam 125 and the probe beam 130 may be coaxially positioned. During operation, the biological specimen 170 can be mounted on a two-dimensional scanning stage with a minimal step size, for example $\lambda/2$. By raster scanning the biological specimen 170 and recording the time-resolved photoacoustic signal at each scanning point, three-dimensional information of the biological specimen 170 may be stored and three-dimensional PAT images can be reconstructed based on the acquired data. Tomographic images can be rendered in various forms, such as cross section, simple back-projection, filtered back-projection, and other modified back-projection methods. The reconstruction of tomographic images can be performed in the time domain or the frequency domain. Additionally, signal processing methods can be applied to improve the imaging quality before or after the reconstruction.

Figure 6:
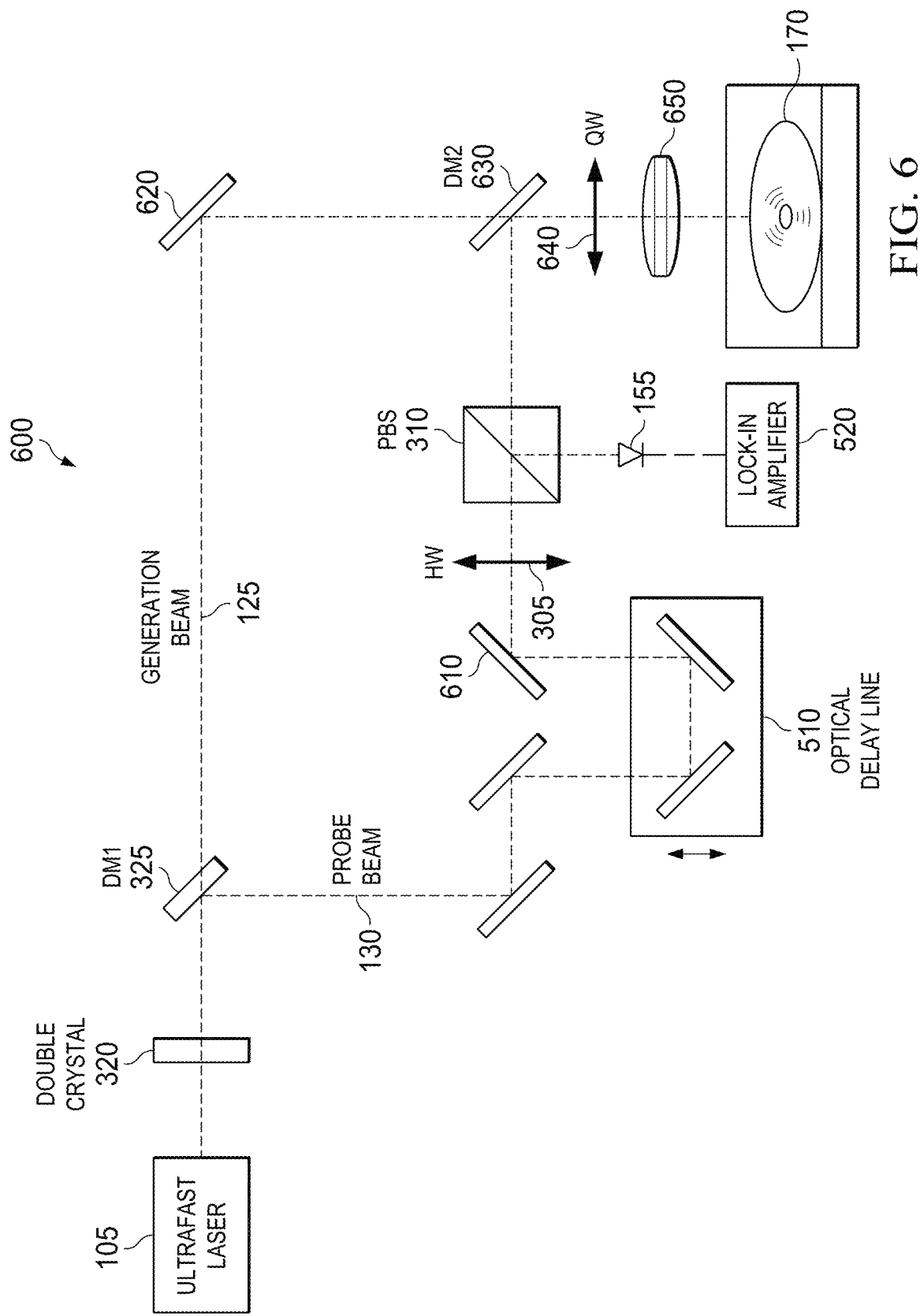
FIG. 6 shows a schematic of an embodiment of an nPAT system which forms synchronous generation and probe beams based on frequency doubling.

FIG. 6 shows the configuration of an alternate embodiment of the nPAT system 600 wherein the generation beam 125 and probe beam 130 are synchronous but have different wavelengths. In this embodiment, the nPAT system 600 is configured in a reflection scheme. The laser emitting beam first passes through a double crystal 320 to produce a second harmonic beam with a specified conversion efficiency, e.g. 10% for BBO. After the double crystal 320, the fundamental ($\lambda_1$) and second harmonic ($\lambda_2=\lambda_1/2$) beams are co-axial and separated by a first DM, DM1 325. In one sample embodiment, the long pass dichroic mirror DMLP650, which is cutoff at 650 nm, can be used for the fundamental wavelength of $\lambda_1=1064$ nm. The fundamental (generation) beam 125 passing through the DM1 325 is directed by a reflecting mirror 620, and focused onto the biological specimen 170 after transmitting a second DM, DM2 630. The second harmonic (probe) beam 130 is reflected by the DM1 325 and enters the optical delay line 510 for adjustment of its optical path length, and the output beam is steered by a reflecting mirror 610. To control the power of the probe beam 130 for detection, a combination of an HW plate 305 and PBSs 310 is adopted. By rotating the HW plate 305, the polarization of the probe beam 130 can be controlled and the transmission of beam is adjusted by the PBS 310. Meanwhile, the separation of probe (incident) beam 130 and backscattered light from the probe beam 130 can be achieved by inserting a QW plate 640 between DM2 630 and objective lens (e.g., second focusing assembly) 650. Here, the PBS 310 is also used to separate the backscattered light and the probe beam 130. Since the backscattered light passes through the QW plate 640 twice, its polarization has changed and it is reflected by the PBS 310. Then, the backscattered light (reflected probe beam light) is recorded by an optical detector 155 and corresponding signals are sent to the lock-in amplifier 520. As in the first embodiment, a time-resolved photoacoustic signal can be measured by manually tuning or automatically scanning the optical delay line 510, and recording the output of the lock-in amplifier 520.

Figure 7:
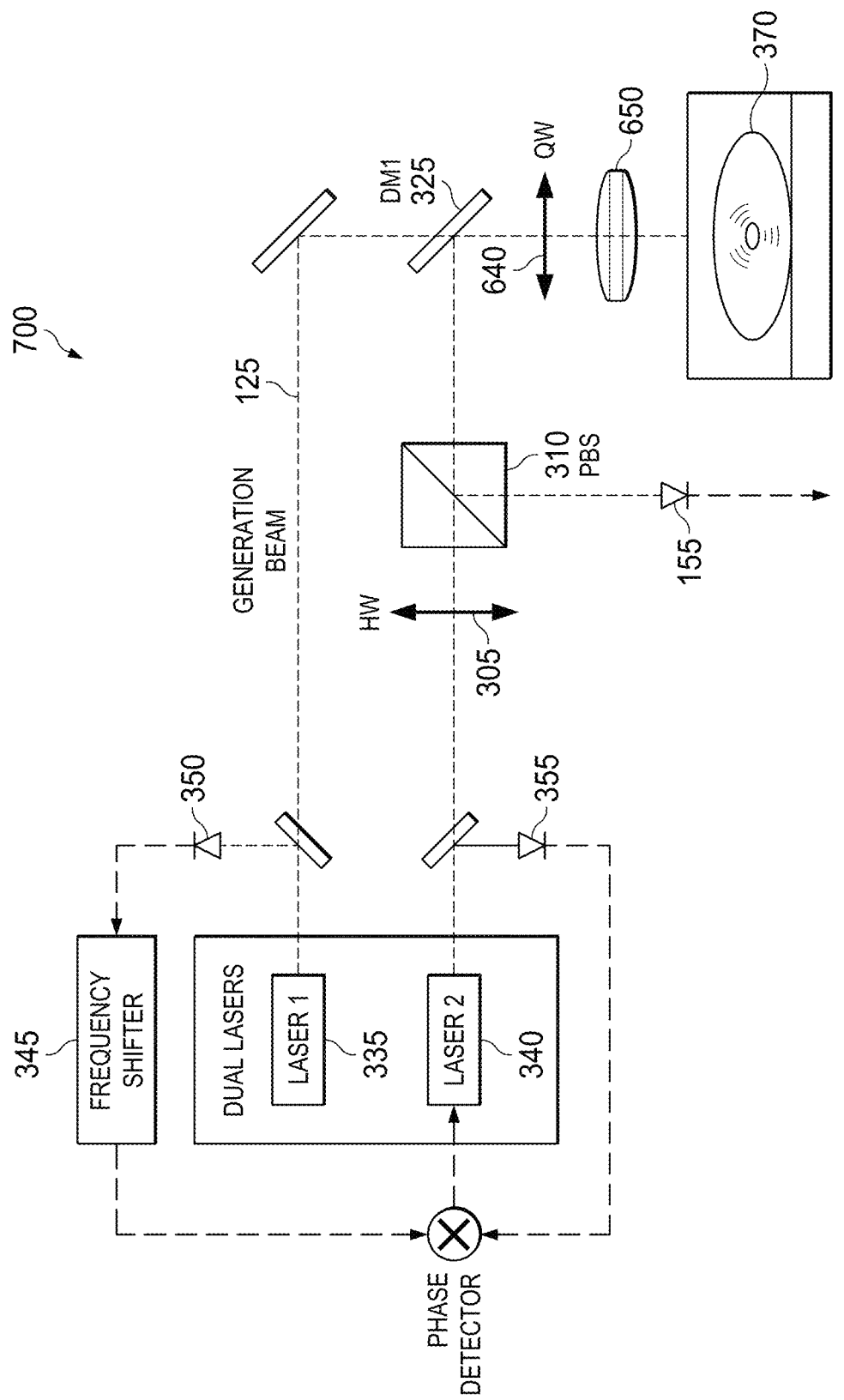
FIG. 7 shows a schematic of an embodiment of an nPAT system which forms asynchronous generation and probe beams.

FIG. 7 shows the configuration of a third embodiment of the nPAT system 700 with dual laser heads (the generation beam 125 and the probe beam 130 are asynchronous from a different laser source and may have different wavelengths). The generation beam 125 from laser 1 335 with wavelength $\lambda_1$ is reflected by a mirror (ref no.?) and transmitting a first DM, DM1 325. The probe beam 130 from laser 2 340 with wavelength $\lambda_2$ (which may be the same or different from $\lambda_1$) passes through the HW plate 305 and the PBS 310, and the transmitted energy can be set by rotating the HW plate 305. Then, the generation beam 125 and the probe beam 130 are combined together with DM1 325 and focused by an objective lens 650 onto the biological specimen 370. As in previous embodiments, a QW plate 640 is inserted between the objective lens 650 and the PBS 310 to separate the probe beam 130 and the backscattered light. The backscattered light is recorded by the optical detector 155. In this embodiment, the delay time is derived based on asynchronous optical sampling as indicated in FIG. 4, different from previous embodiments based on mechanical scanning. The difference of repetition frequencies between laser 1 and laser 2 can be controlled by a frequency shifter, and therefore the time resolution and measurement time for time-resolved photoacoustic waves could be adjusted, which are dependent on the repetition frequency difference. The maximum delay time is determined by the repetition frequency of the generation beam 125, which also has an effect on the time-resolution. For this embodiment, the imaging speed and the maximum delay time may be superior over certain other embodiments based on mechanical scanning. However, the time-resolution is poorer than that of mechanical scanning, which is up to 1.67 fs, and the detection sensitivity may be another disadvantage without the help of a lock-in amplifier.

An advantage of the nPAT system and method disclosed herein is that three-dimensional nanoscale information can be obtained on a point-by-point basis by non-invasive use of non-ionizing radiation. The nPAT system provides a combination of high optical contrast and high ultrasonic resolution, and may also provide functional imaging ability at a subcellular level, manifesting concentrations and changes of the biological substances in the localized areas in the specimen with both high sensitivity and high specificity.

The biological specimen which is subjected to the nPAT system, in certain embodiments, can be mounted on a translation stage which may have a motorized scanning stage. The nPAT system may be equipped with a scanning stage to perform raster scanning in the horizontal plane. Raster scanning may be performed at any desired step size, and a particularly suitable step size may be the half wavelength of the illuminating laser. Other suitable step sizes may be, for example, from about 10 nm to about 1000 nm. While the scanning stage performs raster scanning in the horizontal plane, a manual vertical translator may be used for manual focusing of the light collecting lens assembly.

The demodulated photoacoustic signals from the lock-in amplifier can be digitized, for example, by a 16-bit, 100 MHz data acquisition card and collected and interpreted by a processor. The processor may record acquired signals at each delay time, forming photoacoustic time history at each scanning point. With raster scanning (imaging in x-y plane) and time delay scanning (imaging z-axis), the tomographic image is formed from the time-resolved photoacoustic signals.

In another non-limiting use, the nPAT system can be used for mapping nanoscale subcellular structures in a biological specimen. The method includes exposing the biological specimen to an ultrashort pulse light (generation beam), wherein the light is focused onto an area of the specimen with a focusing assembly; transforming optical energy absorbed by the specimen in response to the pulse light into a photoacoustic wave according to thermal expansion; detecting changes in reflectivity due to the photoacoustic wave using a probe beam with adjustable delay time; and creating a three dimensional tomographic image of the localized area of the specimen using a processor, the image being representative of information derived from the photoacoustic waves.

In at least certain embodiments, the present disclosure is directed toward label-free, non-contact, and non-invasive imaging of subcellular structures of a biological sample (a.k.a., specimen). The biological sample may be examined ex vivo or in vivo. The term "label-free" is used according to its ordinary meaning as understood to mean that the imaging can be performed based on the intrinsic optical properties in the specimen without applying a labeling agent to enhance or provide contrast. The term "label" as used herein is also intended to include stains, markers, probes, dyes, and ligands used as contrast agents in other imaging techniques. The term "non-contact" means that imaging can be performed without any couplant such as is required in transducer based photoacoustic tomographic and microscopy. The term "non-invasive" means no component of the nPAT system is introduced internally into the portion of the biological sample being imaged. The term "in vivo" is used herein according to its ordinary meaning as understood to mean the biological sample in its normal, intact state. The term "ex vivo" is used to refer to a biological sample in an artificial environment, with the minimum alteration of natural conditions. The ex vivo biological sample can be, for example, an intact cell removed from tissue, but not further processed. The ex vivo biological sample may further be histologically processed.

While generally described herein as imaging nanoscale subcellular structures in the biological specimen, it should be understood that the nPAT systems and methods disclosed herein are not limited to imaging at the nanoscale level (e.g., 0.1 nm to 100 nm), but can also be conducted at the microscale level (e.g., 0.1 µm to 100 µm) when a suitable pulse width is used, for example for imaging tissues and organs.

The nPAT system and method disclosed herein may further present mechanical contrast in biological specimens and probe the specimen's acoustic properties, including thickness, density, acoustic velocity, elasticity, and attenuation, etc. The spatial resolution of ultrasound images is similar to that of photoacoustic images and higher than that of optical images. Accordingly, the photoacoustic, optical, and ultrasound imaging results of the same sample may be combined together through image registration and used to provide very comprehensive diagnostic information.

In addition, the nPAT system and method disclosed herein can extract complementary information of biological specimens that may describe subcellular structures and properties based on both optical and acoustic contrast. Optical contrast may present the physiology and biochemical properties of biological specimens at molecular levels, and ultrasound images on mechanical properties may be added to achieve a more comprehensive diagnosis, with high spatial and temporal resolution as well as high sensitivity and specificity.

The present disclosure demonstrates a novel method and system that is useful for imaging of biological specimens with nanoscale (or microscale) resolution. In at least certain embodiments, the nPAT described herein is a non-invasive and label-free method for acquiring subcellular structural information with strong optical contrast and high spatial and temporal resolution, based on optical excitation and detection. For example, it enables determination of shape, size, and distributions of many of the structures within the cell. Therefore, nPAT has broad applications in cancer cell studies and diagnosis.

Example

In one non-limiting example of an nPAT system of the present disclosure, the lateral resolution of the nPAT system may be determined by the optical diffraction, and the lateral FWHM is 0.51λ/NA, where λ is the wavelength of a generation beam, and NA is the numerical aperture of an objective lens. In conventional PAM, an ultrasonic transducer is used to receive the generated photoacoustic signals, and the axial resolution is determined by the transducer bandwidth. Since a coupling medium is required in conventional PAM, the high frequency components are attenuated, reducing the bandwidth of received photoacoustic signals. Moreover, the central frequency and bandwidth of the commercial transducer is limited. The best axial resolution obtained is usually in the micrometer range, even with a state-of-art transducer up to 2 GHz. However, this is not the case for the nPAT system according to the present disclosure, in which the bandwidth is unlimited and the axial resolution is determined by the generated photoacoustic signal itself. For verification, a FEM simulation on the photoacoustic generation with an ultrashort pulse is performed, and the axial resolution is evaluated according to both the frequency spectrum and envelop of the generated photoacoustic wave. Meanwhile, a simulation of B-scan nPAT with two nanoparticles is performed for demonstrating the feasibility of the present method and system for nano-tomography.

Figure 8:
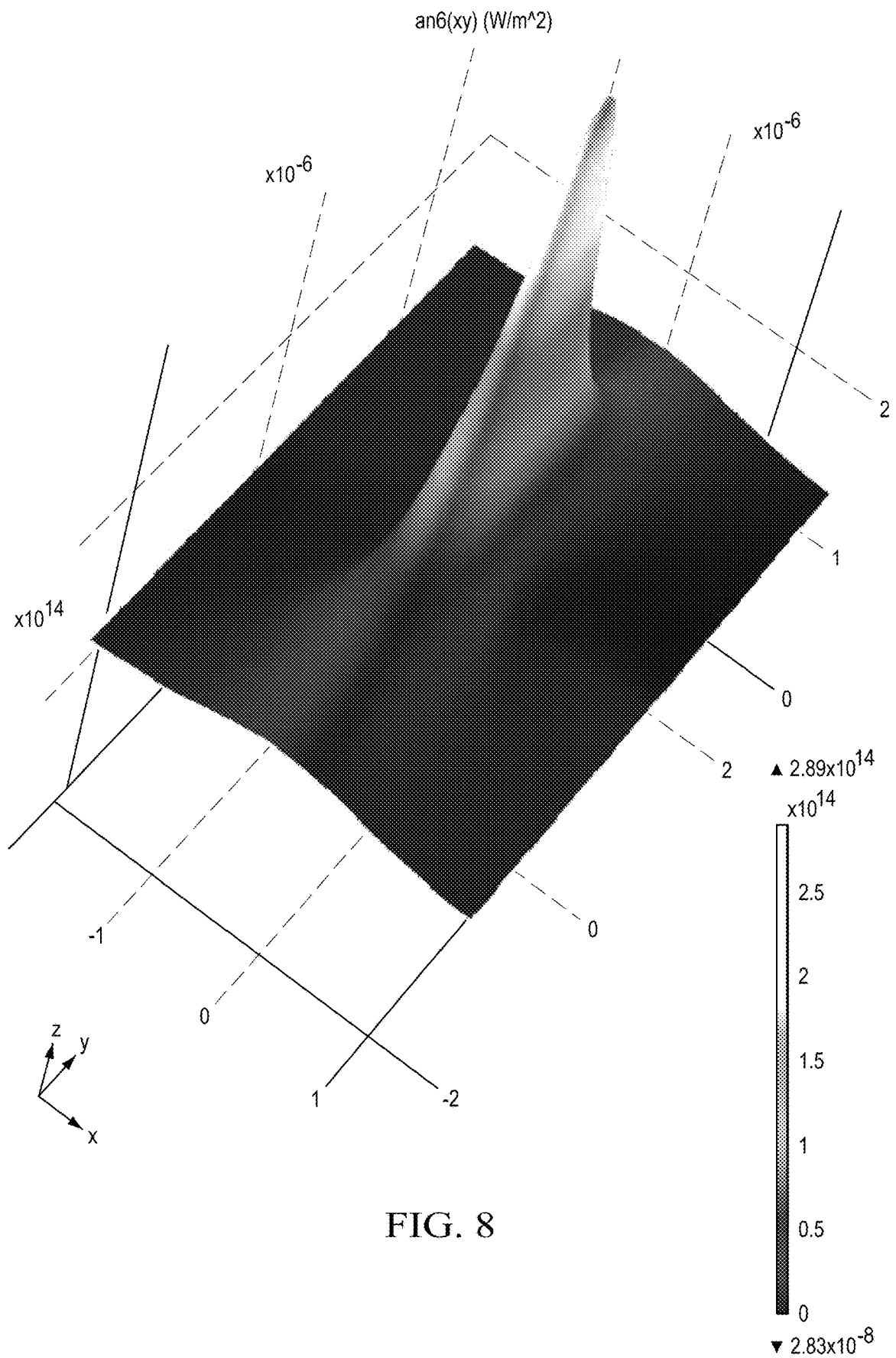
FIG. 8 is a graphical depiction of a profile of Gaussian beam for simulation.

In the simulation, a focusing Gaussian laser beam is applied, with beam waist diameter of $e^{-2}$ radius of $w_0$ in intensity. The beam waist diameter is related to FWHM, and is given by:

$$w_0 = \frac{1}{\sqrt{2\ln 2}} FWHM = \frac{\lambda}{2.35 NA},$$

where λ is 532 nm, and NA is 0.7. Thus, the diameter of the spot size is set to $2w_0$=647 nm and the optical section is $2\pi w_0^2/\lambda$=1.24 um. For illustration, the profile of a Gaussian beam is shown in FIG. 8.

Figure 9:
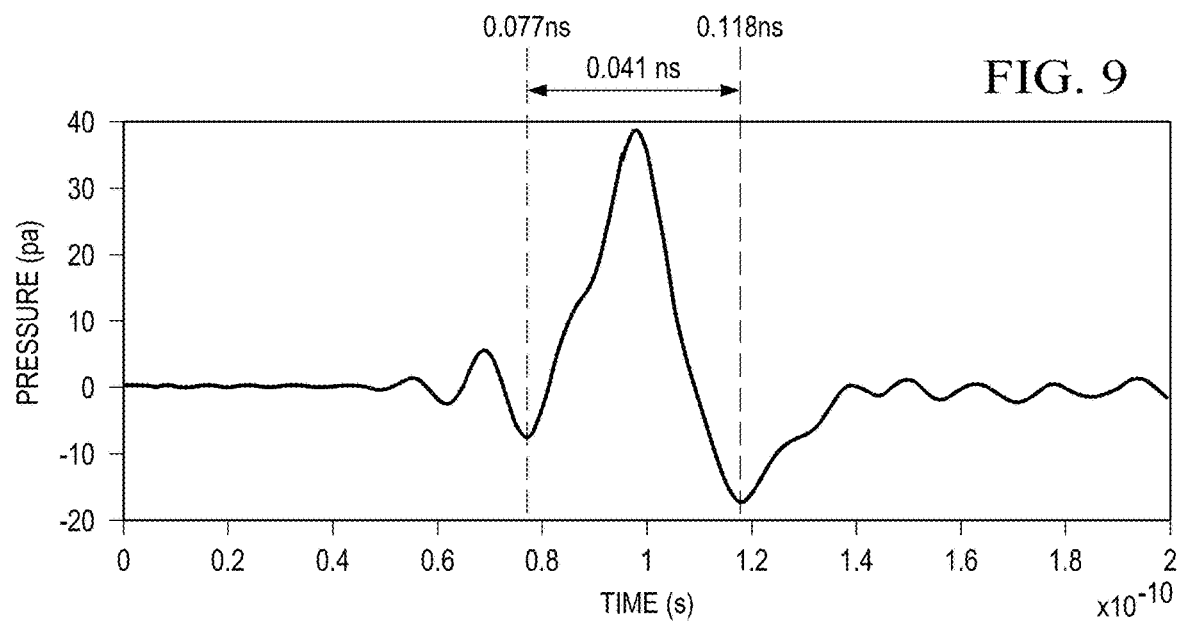
FIG. 9 is a graphical depiction of a time-resolved photoacoustic waveform.

According to the Gaussian beam setting, the simulation is carried out in a rectangular area by 10×30 µm², and the beam waist is centered laterally in the simulation area. The specimen used in the simulation is a 200-nm-diameter titanium microsphere immersed in water. For forward photoacoustic simulation, the duration of a laser pulse is 5 ps, and the time step chosen is 0.5 ps with a total of 40,000 time steps. To record the generated photoacoustic waves, a point probe is used and is located at a distance of 20 µm from the microsphere center. Based on the simulation results, the recorded time-resolved photoacoustic waveform is plotted in FIG. 9, and the duration of the photoacoustic pulse is determined to be 41 ps.

Figure 10:
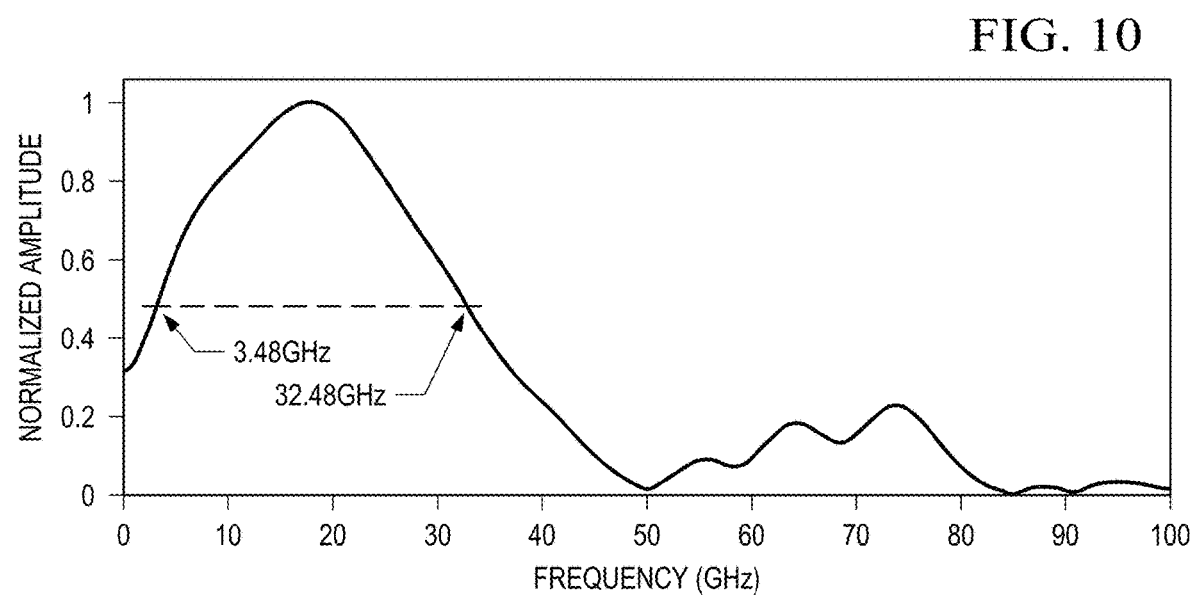
FIG. 10 is a graphical depiction of a frequency spectrum of generated photoacoustic waves.

The frequency spectrum of the generated photoacoustic wave is shown in FIG. 10. The FWHM of the spectrum is 29 GHz. Since the bandwidth of the system is unlimited, the axial resolution is determined by the FWHM of the photoacoustic spectrum, which is given as Δz=0.88 c/BW. The acoustic velocity of water in room temperature (293.15 K) is 1482 m/s, and Δz is calculated to be 45 nm. Therefore, the axial resolution of 45 nm is achievable according to the present disclosure, which is much smaller than that of the conventional PAM and optical sectioning.

Figure 11:
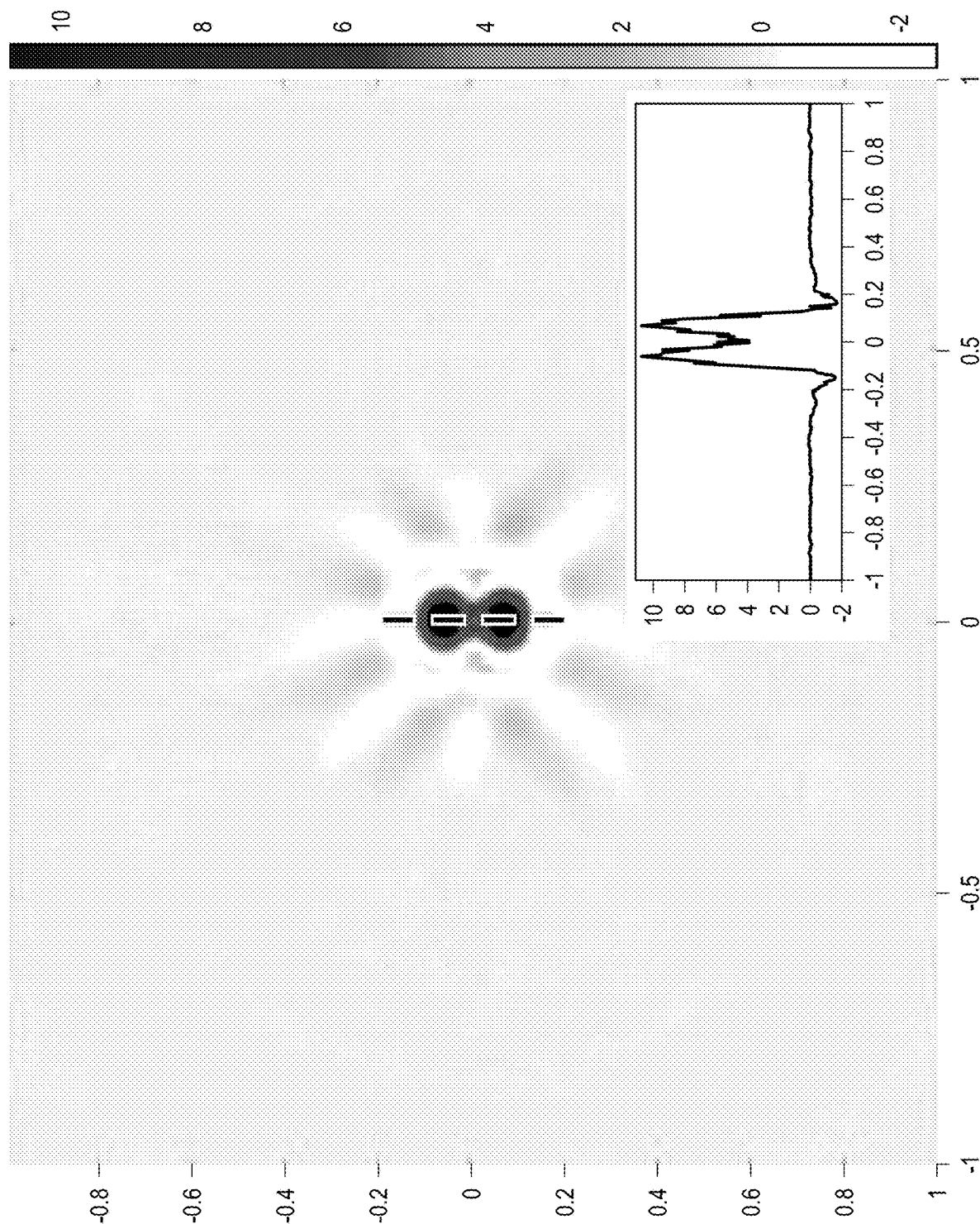
FIG. 11 shows a simulated B-scan photoacoustic micrograph of two gold nanoparticles.

To further demonstrate the resolving capability of nPAT, a B-scan PAM of two gold nanoparticles is illustrated in FIG. 11. The diameter of nanoparticles is 100 nm and the distance between them is 20 nm. For a better view, a 2×2 µm² around the Gaussian foci is selected and an amplitude profile along the dashed lines is plotted. From the simulated B-scan PAM image, the two particles can be clearly resolved.

A first component is directly coupled to a second component when there are no intervening components, except for a line, a trace, or another medium between the first component and the second component. The first component is indirectly coupled to the second component when there are intervening components other than a line, a trace, or another medium between the first component and the second component. The term "coupled" and its variants include both directly coupled and indirectly coupled.

The apparatus, systems and methods disclosed herein can be made and executed without undue experimentation in light of the present disclosure. While the present disclosure has been described in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure. Thus the examples described above, which include particular embodiments, will serve to illustrate the practice of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the presently disclosed apparatus, systems and methods. Changes may be made in the apparatus, systems and methods, or in the steps or the sequence of steps of the methods described herein without departing from the spirit and scope of the present disclosure.

What is claimed is:

1. A nanoscale photoacoustic tomography system comprising:
    an ultrafast pulse laser system configured to:
        provide a generation beam for generating photoacoustic waves in a biological sample, wherein the generation beam is a generation light beam, and wherein the generation beam has a pulse duration in a range of about 100 femtoseconds (fs) to about 100 picoseconds (ps); and
        provide a probe beam for assessing changes in light reflectivity in the biological sample caused by the photoacoustic waves, wherein the probe beam is a probe light beam that is separate from the generation light beam, and wherein the probe beam has the pulse duration;
    a scanning stage configured to mount the biological sample for analysis;
    a first focusing assembly configured to focus the generation beam on the biological sample;
    a second focusing assembly configured to:
        focus the probe beam on the biological sample; and
        collect backscattered light reflected from the biological sample;
    an optical detector configured to:
        sense the backscattered light; and
        emit signals in response to the backscattered light; and
    a processor configured to record and process the signals.

2. The nanoscale photoacoustic tomography system of claim 1, wherein the first focusing assembly comprises a first microscope objective lens configured to focus the generation beam to a substantially diffraction-limited spot, and wherein the second focusing assembly comprises a second microscope objective lens.

3. The nanoscale photoacoustic tomography system of claim 1, wherein the second focusing assembly comprises an assembly of lenses and mirrors configured to receive the backscattered light.

4. The nanoscale photoacoustic tomography system of claim 1, wherein the ultrafast pulse laser system comprises a common laser configured to emit the probe beam and the generation beam.

5. The nanoscale photoacoustic tomography system of claim 1, further comprising:
    a polarization beam splitter (PBS) configured to pass the probe beam and the backscattered light; and
    a quarter wave (QW) plate coupled to the PBS configured to pass the probe beam and the backscattered light.

6. The nanoscale photoacoustic tomography system of claim 1, further comprising an amplifier configured to amplify the signals.

7. The nanoscale photoacoustic tomography system of claim 1, wherein the scanning stage is an XY scanning stage configured to perform nanometer step size raster scanning.

8. The nanoscale photoacoustic tomography system of claim 1, wherein the ultrafast pulse laser system comprises a beam splitter configured to:
    emit a laser beam; and
    split the laser beam into the generation beam and the probe beam.

9. The nanoscale photoacoustic tomography system of claim 1, further comprising a time delay adjustment mechanism configured to introduce or modify a time delay between the generation beam and the probe beam.

10. The nanoscale photoacoustic tomography system of claim 9, wherein the nanoscale photoacoustic tomography system is configured to iteratively tune the delay time and record corresponding signals to measure a time-resolved photoacoustic signal.

11. The nanoscale photoacoustic tomography system of claim 1, wherein the ultrafast pulse laser system comprises a first laser configured to emit the probe beam and a second laser configured to emit the generation beam.

12. The nanoscale photoacoustic tomography system of claim 1, wherein the probe beam is configured to be absorbed by the biological sample to cause the biological sample to propagate photoacoustic waves, thereby inducing the changes, and wherein the backscattered light is based on the changes and reflection of the probe beam from the biological sample.

13. The nanoscale photoacoustic tomography system of claim 12, wherein the backscattered light is not based on reflection of the generation beam from the biological sample.

14. The nanoscale photoacoustic tomography system of claim 1, wherein the generation beam and the probe beam are synchronous and of a same wavelength.

15. The nanoscale photoacoustic tomography system of claim 1, wherein the generation beam and the probe beam are synchronous and of a different wavelength.

16. The nanoscale photoacoustic tomography system of claim 1, wherein the generation beam and the probe beam are asynchronous and of a different wavelength.

17. A method of nanoscale photoacoustic tomography comprising:
    emitting, using an ultrafast pulse laser system, a generation beam for generating photoacoustic waves in a biological sample and a probe beam for assessing changes in light reflectivity in the biological sample, wherein the generation beam is a generation light beam, wherein the probe beam is a probe light beam that is separate from the generation light beam, and wherein the generation beam and the probe beam have a pulse duration in a range of about 100 femtoseconds (fs) to about 100 picoseconds (ps);
    illuminating the biological sample with the generation beam to form the photoacoustic waves in the biological sample, wherein the photoacoustic waves cause changes in the light reflectivity of the biological sample;
    illuminating the biological sample with the probe beam at a predetermined delayed time after illuminating the biological sample with the generation beam;

detecting, via an optical detector, backscattered light reflected from the biological sample after illumination with the probe beam; and recording and processing signals from the optical detector to form an image of at least a portion of the biological sample.

18. The method of claim 17, further comprising:

using a first focusing assembly to focus the generation beam on a substantially diffraction-limited location on the biological sample; and using a second focusing assembly to focus the probe beam.

19. The method of claim 17, further comprising further emitting the probe beam and the generation beam using a common laser source or using separate laser sources.

20. The method of claim 17, further comprising passing the probe beam and the backscattered light through a polarization beam splitter and a quarter wave plate.

21. The method of claim 17, further comprising splitting a laser beam into the generation beam and the probe beam via a beam splitter.

22. The method of claim 17, further comprising tuning a wavelength of the generation beam.

23. The method of claim 17, further comprising introducing or modifying the predetermined delayed time via a time delay adjustment mechanism.

24. The method of claim 17, further comprising adjusting the predetermined delayed time by mechanical scanning of an optical delay line or by optical sampling.

25. A nanoscale photoacoustic tomography system comprising:

an ultrafast pulse laser system configured to:

provide a generation beam for generating photoacoustic waves in a biological sample, wherein the generation beam is a generation light beam, and wherein the generation beam has pulse duration in a range of about 100 femtoseconds (fs) to about 100 picoseconds (ps); and provide a probe beam for assessing changes in light reflectivity in the biological sample caused by the photoacoustic waves, wherein the probe beam is a probe light beam that is separate from the generation light beam, and wherein the probe beam has the pulse duration;

a scanning stage configured to mount the biological sample for analysis;

an objective lens configured to:

focus the generation beam on the biological sample;

focus the probe beam on the biological sample; and collect backscattered light reflected from the biological sample; and an optical detector configured to:

sense the backscattered light; and emit signals in response to the backscattered light.

26. The nanoscale photoacoustic tomography system of claim 25, further comprising a polarization beam splitter (PBS) and a quarter wave (QW) plate coupled to the objective lens and configured to separate the probe beam and the backscattered light.

27. The nanoscale photoacoustic tomography system of claim 25, wherein the generation beam and the probe beam are asynchronous and of a different wavelength.

28. The nanoscale photoacoustic tomography system of claim 27, wherein the nanoscale photoacoustic tomography system is configured to iteratively tune the delay time and record corresponding signals to measure a time-resolved photoacoustic signal.

* * * * *